US00PP22470P2

(12) United States Plant Patent
Meilland

(10) Patent No.: US PP22,470 P2
(45) Date of Patent: Jan. 31, 2012

(54) CLIMBING ROSE PLANT NAMED 'MEITERATOL'

(50) Latin Name: *Rosa hybrida*
Varietal Denomination: Meiteratol

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/923,055

(22) Filed: Aug. 31, 2010

(51) Int. Cl.
*A01H 5/00* (2006.01)

(52) U.S. Cl. ..... Plt./109
(58) Field of Classification Search ..... Plt./109
See application file for complete search history.

*Primary Examiner* — Kent L Bell
(74) *Attorney, Agent, or Firm* — Buchanan Ingersoll & Rooney PC

(57) ABSTRACT

A new and distinct variety of rose plant is provided which forms in abundance on a substantially continuous basis beginning in the spring attractive very double blossoms wherein the petal coloration is intense red-purple streaked with lighter red-purple. A very strong climbing growth habit is displayed. Commonly few thorns are present. Attractive very dense dark green foliage is formed having a glossy upper surface. Good disease tolerance has been observed. The new variety is particularly well suited for growing as distinctive colorful ornamentation in parks, gardens, and residential settings.

1 Drawing Sheet

Figures 1, 2, 3, 4, 5, 6, 7, 8, 9, 10, 11, 12, 13, 14, 15, 16:
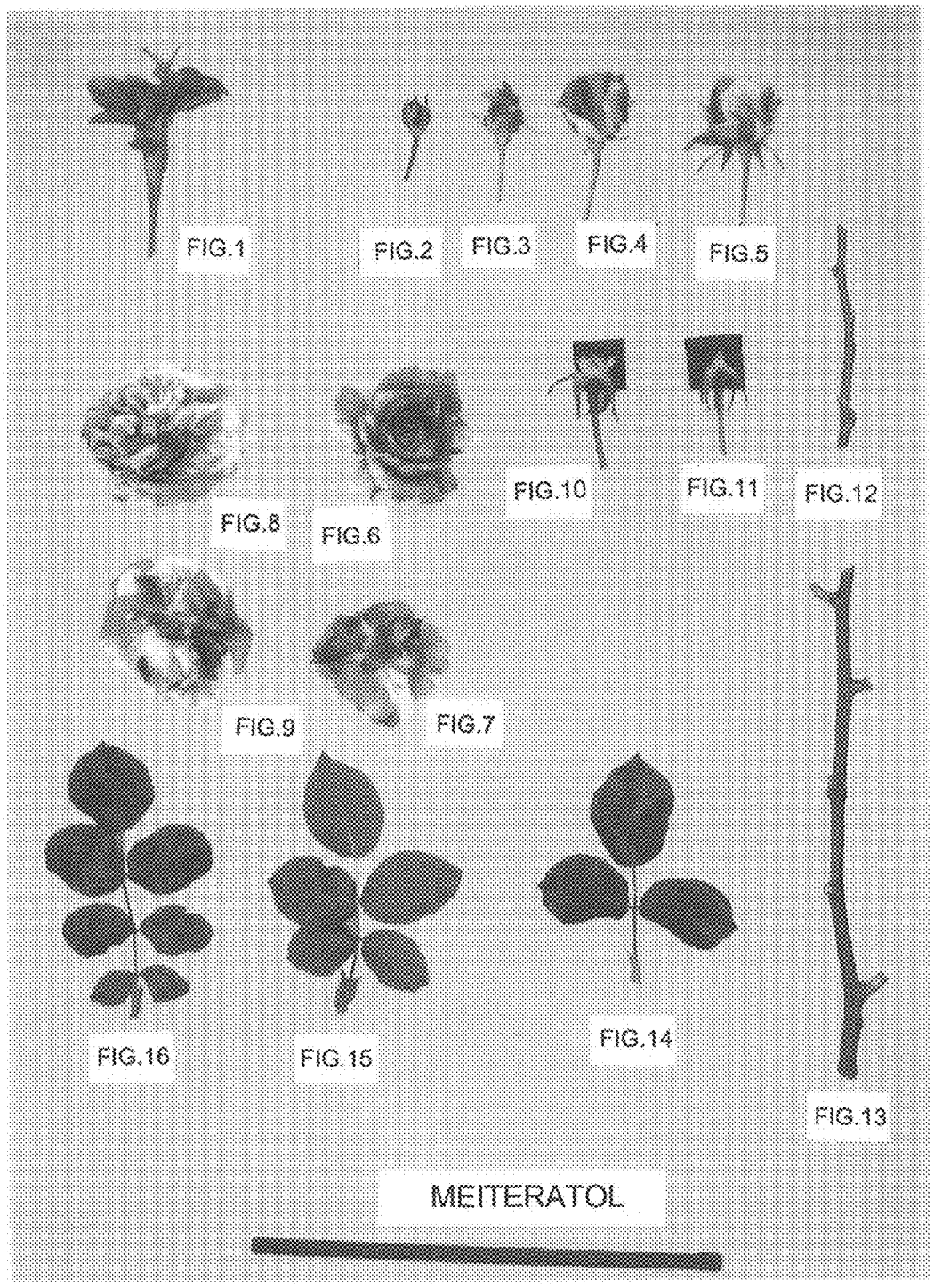

Botanical/commercial classification: *Rosa hybrida*/Climbing Rose Plant.
Varietal denomination: cv. Meiteratol.

SUMMARY OF THE INVENTION

The new variety of *Rosa hybrida* Climbing rose plant of the present invention was created at Le Cannet-Des-Maures, Var, France, by artificial pollination wherein two parents were crossed which previously had been studied in the hope that they would contribute the desired characteristics. The female parent (i.e., the seed parent) was the 'Meinoiral' variety (non-patented in the United States). The male parent (i.e., the pollen parent) of the new variety was the product of the cross of the 'Meihestries' variety (non-patented in the United States) and the 'Meidomonac' variety (U.S. Plant Pat. No. 5,105). The parentage of the new variety can be summarized as follows:

'Meinoiral'×('Meihestries'×'Meidomonac').

The seeds resulting from the above pollination were sown and small plants were obtained which were physically and biologically different from each other. Selective study resulted in the identification of a single plant of the new variety.

It was found that the rose plant of the present invention possesses the following combination of characteristics:

(a) abundantly and substantially continuously forms attractive very double blossoms wherein the petal coloration is intense red-purple streaked with lighter red-purple,
(b) exhibits a very strong climbing growth habit and commonly, bears few thorns,
(c) forms attractive very dense dark green foliage with a glossy upper surface,
(d) displays good disease tolerance, and
(e) is well suited for providing distinctive colorful ornamentation.

The new variety displays good repeat blooming beginning in the spring. The intense red-purple blossoms contrast nicely with the glossy dark green foliage. Commonly the thorns are present at a somewhat sparse frequency.

The new variety well meets the needs of the horticultural industry. It can be grown to advantage as an attractive Climber in parks, gardens, public areas, and in residential settings. The new variety is particularly well suited for providing attractive colorful ornamentation.

The new variety of the present invention can be readily distinguished from its ancestors, as well as other climbing rose varieties that are available to others for comparison, such as the 'Meivalier' variety (non-patented in the United States). More specifically, the 'Meinoiral' variety forms clear medium pink blossoms. The 'Meihestries' variety forms striped red blossoms having a substantially lesser number of petals. The 'Meidomonac' variety forms light pink blossoms also having a substantially lesser number of petals. The 'Meivalier' variety, unlike the previously identified varieties, is a Climber and forms dissimilar blossoms that are light orange to golden in coloration. The male parent formed by the cross of the 'Meihestries' variety and 'Meidomonac' variety was not released to the public and no longer exists. Accordingly, the male parent is not available for comparative purposes.

The characteristics of the new variety have been found at Le Cannet-Des-Maures, Le Luc, France, to be homogeneous and stable and to be strictly transmissible by asexual propagation, such as budding, grafting, and the rooting of cuttings, from one generation to another. Accordingly, the new variety reproduces in a true-to-type manner by such asexual propagation.

The new variety has been named 'Meiteratol'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during August while growing outdoors on *Roas laxa* understock at LeCannet-des-Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower during the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates specimen of a leaf with five leaflets — plan view — under surface; and FIG. 16 — illustrates a specimen of a leaf with seven leaflets — plan view — upper surface.

DETAILED DESCRIPTION

The chart used in the identification of colors is that of The Royal Horticultural Society (R.H.S. Colour Chart), London, England. The description is based on the observation of one-year-old specimens of the new variety during October while growing on *Rosa laxa* understock outdoors at Le Cannet-Des-Maures, Var, France.

Class: Climbing Rose.

Plant:

*Habit.*—Climbing.

Branches:

*Length.*—Typically approximately 1.1 m on average.

*Diameter.*—Typically approximately 9 mm on average.

*Internode length.*—Typically approximately 3.2 cm on average.

*Color.*—Young stems: commonly near Yellow-Green Group 144A. adult wood: commonly near Yellow-Green Group 144A.

*Thorns.*—Size: commonly approximately 7 to 9 mm in length on average on adult stems. configuration: elongated and curved downwards on the upper surface, and slightly concave on the under surface with an obovate and narrow base. quantity: commonly 3 or 4 on average over a length of 10 cm. color: Greyed-Orange Group 166C.

Leaves:

*Leaflet number.*—3, 5, 7 (most often), and 9.

*Leaflet texture.*—On the upper side generally is smooth with an indentation towards the midvein, and leathery.

*Leaflet shape.*—Generally oval with an acuminate apex and a rounded base.

*Leaflet margins.*—Finely denticulate.

*Leaflet size.*—A terminal leaflet commonly is approximately 8.5 cm in length on average, and approximately 8 cm in width on average at the widest point.

*Overall appearance.*—Very dense, dark green with a glossy finish.

*Color.*—Young leaves: upper surfaces commonly are near Green Group 137B, and under surfaces commonly are near Yellow-Green Group 148C. adult leaves: upper surfaces commonly are near Green Group 137A, and under surfaces commonly are near Yellow-Green Group 147C.

*Stipules.*—Adnate, pectinate, rather broad, approximately 1.4 cm in length on average, approximately 6 mm in width on average, on the upper surface near Yellow-Green Group 146C in coloration, and on the under surface near Yellow-Green Group 146D in coloration.

*Petiole.*—On the upper surface non-glandular, on the under surface bear a few prickles, approximately 1.7 cm in length on average on a terminal leaflet, on the upper surface near Yellow-Green Group 146C in coloration, and on the under surface near Yellow-Green Group 146D in coloration.

*Rachis.*—Commonly approximately 7.8 cm in length on average, approximately 2 mm in diameter on average, on the upper surface near Yellow-Green Group 146C in coloration, and on the under surface near Yellow-Green Group 146D in coloration.

Inflorescence:

*Bearing.*—Commonly in clusters of on average approximately 7 to 12 blossoms per stem.

*Peduncle.*—Smooth, commonly approximately 4.5 cm in length on average, approximately 3 mm in diameter on average, and near Yellow-Green Group 147D in coloration commonly with light anthocyanin suffusion of Greyed-Red Group 178B.

*Sepals.*—Shape: longish pointed, and generally upright at the base. length: commonly approximately 2.5 cm on average. width: commonly approximately 8 to 10 mm on average at the base. margin: commonly two sepals have entire margins, commonly two sepals have extensions on both edges measuring approximately 4 mm in length, and commonly one sepal has extensions on only one edge measuring approximately 4 mm in length. number five. texture: the inner surface commonly is tomentose, and near Yellow-Green Group 147D in coloration, and the outer surface commonly is smooth and near Green Group 138B in coloration.

*Buds.*—Shape: commonly conical. length: as the calyx breaks commonly approximately 2 cm on average. diameter: as the calyx breaks commonly approximately 2 cm on average at the widest point. color (as the calyx breaks): upper surface: near Red-Purple Group 66A, and more or less streaked with lighter Red-Purple Group 62A, 62B, and 62C. under surface: near Red-Purple Group 67A, and more or less streaked with Red-Purple Group 62B.

*Flower.*—Form: very double. configuration: cup-shaped. diameter commonly approximately 8 to 10 cm on average when fully open. color (in course of opening): upper surface: near Red-Purple Group 66A and more or less streaked with lighter near Red-Purple Group 62A, with a spot of near Yellow Group 2C at the base. under surface: near Red-Purple Group 66A and more or less streaked with lighter near Red-Purple Group 62B and 62C, with a spot of near Yellow Group 2D at the base. color (open flower): upper surface: near Red-Purple Group 64B and more or less streaked with lighter Red-Purple Group 62B and 62C, with a spot of near Yellow Group 2C at the base. under surface: near Red-Purple Group 64C and more or less streaked with Red-Purple Group 62B and 62C, with a spot of near Yellow Group 2D at the base. petal number: commonly approximately 100 to 118 on average under normal growing conditions. petal shape: commonly with a reflexed tip and a rounded base. petal apex: obtuse. petal margin: sinuate. petal size: commonly approximately 3.5 cm in length on average, and approximately 3.5 cm in width on average. petal texture: somewhat leathery. petal arrangement: imbricated and commonly without petaloids. fragrance: very slight. petal drop: good, with the petals commonly dropping cleanly and freely before drying. stamen number: commonly approximately 63 on average, and regularly arranged around the pistils. anthers: approximately 2 mm in length on average, and near Yellow-Orange Group 20B in coloration. filaments: commonly approximately 5 mm in length on average, and near Yellow-Orange Group 20B in coloration. pollen: near Yellow-Orange Group 20A in coloration. pistils: commonly approximately 81 on average. styles: commonly approximately 5 mm in length on average, and near Orange-Red Group 33A in coloration. stigma: commonly approximately 2 mm in length on average, and near Yellow Group 13D in coloration.

*Receptacle.*—Generally funnel-shaped in configuration, commonly approximately 7 mm in length on average, commonly approximately 9 to 10 mm in width at the widest point, commonly the surface is smooth, and the coloration commonly is near Yellow-Green Group 147D.

Development:

*Vegetation.*—Very strong.

*Blossoming.*—Abundant and substantially continuous beginning in the spring.

*Tolerance to diseases.*—Good, with no particular disease concerns having been encountered during observations to date.

The new 'Meiteratol' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive very double blossoms wherein the petal coloration is intense red-purple streaked with lighter red-purple, (b) exhibits a very strong climbing growth habit and commonly bears few thorns, (c) forms attractive very dense dark green foliage with a glossy upper surface, (d) displays good disease tolerance, and (e) is well suited for providing distinctive colorful ornamentation; substantially as herein shown and described.

* * * * *

MEITERATOL